(12) United States Patent
Kobayashi et al.

(10) Patent No.: US 9,089,158 B2
(45) Date of Patent: Jul. 28, 2015

(54) ACIDIC OIL-IN-WATER-TYPE EMULSIFIED FOOD, METHOD FOR PRODUCING SAME, ANTIOXIDANT, AND FLAVOR IMPROVING AGENT

(75) Inventors: Hideaki Kobayashi, Tokyo (JP); Ryo Sasahara, Tokyo (JP); Shoichi Yoda, Tokyo (JP); Mari Yamada, Saitama (JP)

(73) Assignee: Q.P. Corporation (JP)

( * ) Notice: Subject to any disclaimer, the term of this patent is extended or adjusted under 35 U.S.C. 154(b) by 1191 days.

(21) Appl. No.: 11/720,682

(22) PCT Filed: Nov. 29, 2005

(86) PCT No.: PCT/JP2005/021885
§ 371 (c)(1),
(2), (4) Date: May 26, 2009

(87) PCT Pub. No.: WO2006/062008
PCT Pub. Date: Jun. 15, 2006

(65) Prior Publication Data
US 2010/0112131 A1 May 6, 2010

(30) Foreign Application Priority Data

Dec. 6, 2004 (JP) .................. 2004-352805
Nov. 17, 2005 (JP) .................. 2005-333058

(51) Int. Cl.
*A23L 1/24* (2006.01)
*A23L 1/305* (2006.01)
(Continued)

(52) U.S. Cl.
CPC ............. *A23L 1/3208* (2013.01); *A23D 7/0053* (2013.01); *A23D 7/06* (2013.01);
(Continued)

(58) Field of Classification Search
CPC .................. A23L 1/24; A23L 3/3472
USPC .......................................... 426/32
See application file for complete search history.

(56) References Cited

U.S. PATENT DOCUMENTS

2002/0197382 A1* 12/2002 Kuijpers et al. ............... 426/603
2003/0165604 A1* 9/2003 Tsubaki et al. ................ 426/549
2004/0067279 A1* 4/2004 Delest et al. .................... 426/42

FOREIGN PATENT DOCUMENTS

JP 51-123849 10/1976
JP 61-005761 1/1986
(Continued)

OTHER PUBLICATIONS

Dávalos et al., "Antioxidant Activity of Peptides Derived from Egg White Proteins by Enzymatic Hydrolysis," Journal of Food Protection, vol. 67, No. 9, 1939-1944 (2004).*
Gülçin et al., "Antiradical and antioxidant activity of total anthocyanins from Perilla pankinensis decne," Journal of Ethnopharmacology, 101 (2005) 287-293.*
(Continued)

*Primary Examiner* — Lien T. Tran
*Assistant Examiner* — Jeffrey Mornhinweg
(74) *Attorney, Agent, or Firm* — Harness, Dickey & Pierce, P.L.C.

(57) ABSTRACT

An acidic oil-in-water-type emulsified food comprising an egg white hydrolyzate. A method of producing the acidic oil-in-water-type emulsified food comprising emulsifying an aqueous phase component and an oil phase component in the presence of the egg white hydrolyzate. An antioxidant comprising an egg white hydrolyzate obtained by treating egg white with a neutral protease originating from a microorganism belonging to the genus *Aspergillus*. A flavor improving agent comprising an egg white hydrolyzate obtained by treating egg white with a neutral protease originating from a microorganism belonging to the genus *Aspergillus*.

20 Claims, 2 Drawing Sheets (51) Int. Cl.

| | |
|---|---|
| *A23L 3/3472* | (2006.01) |
| *A23D 7/06* | (2006.01) |
| *A23L 1/32* | (2006.01) |
| *A23J 3/00* | (2006.01) |
| *C11B 5/00* | (2006.01) |
| *A23D 7/005* | (2006.01) |
| *A23J 3/34* | (2006.01) |
| *A23L 1/227* | (2006.01) |
| *A23L 3/3526* | (2006.01) |

(52) U.S. Cl.
CPC . *A23J 3/04* (2013.01); *A23J 3/341* (2013.01); *A23L 1/227* (2013.01); *A23L 1/24* (2013.01); *A23L 1/3053* (2013.01); *A23L 3/3472* (2013.01); *A23L 3/3526* (2013.01); *C11B 5/0085* (2013.01); *C12Y 304/00* (2013.01); *A23V 2002/00* (2013.01)

(56) References Cited

FOREIGN PATENT DOCUMENTS

| | | |
|---|---|---|
| JP | 61-5761 | 1/1986 |
| JP | 02-218796 | 8/1990 |
| JP | 2-218796 | 8/1990 |
| JP | 07-031415 | 2/1995 |
| JP | 7-31415 | 2/1995 |
| JP | 2004-57123 | 2/2004 |
| JP | 2004-057123 | 2/2004 |
| JP | 2004-180578 | 7/2004 |

OTHER PUBLICATIONS

Sakanaka et al., "Antioxidant activity of egg-yolk protein hydrolysates in a linoleic acid oxidation system," Food Chemistry, 86 (2004) 99-103.*

Mariken, J.T.J. Arts, J. Sebastiaan Dallinga, Hans-Peter Voss, Guido R.M.M. Haenen, Aalt Bast, "A critical appraisal of the use of the antioxidant capacity (TEAC) assay in defining optimal antioxidant structures," Food Chem., 80 (2003) 409-414.*

Huang, D., Ou, B., Prior, R.L., "The Chemistry behind Antioxidant Capacity Assays," J. Agric. Food Chem., 2005, 53, 1841-1856.*

JP02-218796 Translated Excerpt by Irina Knizhnik, USPTO Translator, Dec. 12, 2013.*

JP02-218796 Full Translation by McElroy Translation Company, Jan. 2014.*

Jacobsen, Charlotte, "Lipid Oxidation in Fish Oil Enrichsed Mayonnaise, Calcium Disodium Ethylenediaminetetraacetate", ACS, 49,1009-1019,2001.

Jacobsen, Charlotte, "The Effect of Metal Chelators on Lipid Oxidation in Milk and Mayonnaise", American Oil Chemists Society, 83-84, 2004.

English translation of Chinese Office Action for Application No. 2005-80041804.5 (3 pages) Apr. 2010.

English translation of Chinese Office Action for Application No. 2005-80041804.5 (5 pages) Mar. 2011.

English translation of Japanese Office Action for Application No. 2005-333058, drafted Sep. 7, 2010 (5 pages).

English translation of International Preliminary Report on Patentability for Application No. PCT/JP2005/021885 mailed Feb. 7, 2006 (6 pages).

Korean Office Action for Application No. 10-2007-7015424, mailed Apr. 10, 2012 with English Translation (10 pages).

* cited by examiner

ACIDIC OIL-IN-WATER-TYPE EMULSIFIED FOOD, METHOD FOR PRODUCING SAME, ANTIOXIDANT, AND FLAVOR IMPROVING AGENT

This application claims priority to PCT/JP2005/021885 filed Nov. 29, 2005, Japanese Application No. JP2004-352805 filed Dec. 6, 2004, and Japanese Application No. JP2005-333058 filed Nov. 17, 2005, all of which are incorporated herein by reference in their entireties.

TECHNICAL FIELD

The present invention relates to an acidic oil-in-water-type emulsified food, a method for producing the same, an antioxidant, and a flavor improving agent.

BACKGROUND ART

An acidic oil-in-water-type emulsified food is a food comprising an aqueous phase component and an oil phase component emulsified in an oil-in-water type emulsion. As examples of typical acidic oil-in-water-type emulsified foods, mayonnaise and salad dressings can be given.

Acidic oil-in-water-type emulsified food may change the flavor, deteriorate, or discolor as a result of oxidation of the components during storage. In order to prevent oxidation, a food additive containing a chemical compound such as EDTA Ca.2Na is often added (Charlotte Jacobsen et al., "Lipid Oxidation in Fish Oil Enriched Mayonnaise, Calcium Disodium Ethylenediaminetetraacetate, but Not Gallic Acid, Strongly Inhibited Oxidative Deterioration", Journal of Agricultural and Food Chemistry, American Chemical Society, 49, 1009-1019, 2001; Charlotte Jacobsen et al., "The Effect of Metal Chelators on Lipid Oxidation in Milk and Mayonnaise", 95th AOCS Annual Meeting & Expo, American Oil Chemists' Society, 83-84, 2004).

However, the effects of chemical compounds used as food additives on human bodies are recognized as a problem in recent years. Moreover, consumers have a tendency of avoiding the use of artificial food additives in recent years. For this reason, avoiding the use of chemical compounds in foods as much as possible is desired.

DISCLOSURE OF THE INVENTION

An object of the invention is to provide an acidic oil-in-water-type emulsified food, a method for producing the same, an antioxidant, and a flavor improving agent.

The inventors of the invention have found that oxidation and a change of flavor of an acidic oil-in-water-type emulsified food can be controlled if the food contains an egg white hydrolyzate and have completed the invention based on this knowledge.

An acidic oil-in-water-type emulsified food of the invention comprises an egg white hydrolyzate.

The acidic oil-in-water-type emulsified food of the invention may further comprise egg yolk.

In the acidic oil-in-water-type emulsified food of the invention, the ratio of the mass of the egg white hydrolyzate to the mass of the egg yolk solid component may be 0.01 or more. In the invention, "egg yolk solid component" means the mass of the solid component contained in the egg yolk. The solid component of the egg yolk is usually about 50 mass %. Accordingly, "egg yolk solid component" in the invention means the mass of the solid component in the egg yolk calculated on the basis that the amount of the solid component in the egg yolk is 50 mass %.

In the acidic oil-in-water-type emulsified food of the invention, the egg white hydrolyzate may be obtained by treating the egg white with a neutral protease originating from a microorganism belonging to the genus *Aspergillus*. Here, the egg white hydrolyzate can be obtained by further treating with papain.

In the acidic oil-in-water-type emulsified food of the invention, the egg white hydrolyzate may have the following characteristic: the antioxidant effect of an aqueous solution with an egg white hydrolyzate concentration of 1,000 microgram/ml which is adjusted to a pH of 4 and contains 10 mg/ml (on a solid basis) of egg yolk is equivalent to or more than the antioxidant effect of a 25 nmol/ml aqueous solution of calcium disodium ethylenediaminetetraacetate which is adjusted to a pH of 4 and contains 10 mg/ml (on a solid basis) of egg yolk.

In the acidic oil-in-water-type emulsified food of the invention, the egg white hydrolyzate may contain 0 to 50 mass % of a water-insoluble fraction.

The acidic oil-in-water-type emulsified food of the invention may contain the egg white hydrolyzate in an amount of 0.05 mass % or more.

An method for producing an acidic oil-in-water-type emulsified food of the invention comprises emulsifying an aqueous phase component and an oil phase component in the presence of an egg white hydrolyzate. In the invention, an "aqueous phase component" refers to a component capable of forming an aqueous phase and/or a component dissolvable in the aqueous phase before emulsification. In the invention, an "oil phase component" refers to a component capable of forming an oil phase and/or a component dissolvable in the oil phase before emulsification.

In the method for producing the acidic oil-in-water-type emulsified food of the invention, emulsification may be carried out after adding the egg white hydrolyzate to egg yolk.

An antioxidant of the invention comprises an egg white hydrolyzate obtained by treating egg white with a neutral protease originating from a microorganism belonging to the genus *Aspergillus*.

An flavor improving agent of the invention comprises an egg white hydrolyzate obtained by treating egg white with a neutral protease originating from a microorganism belonging to the genus *Aspergillus*.

BEST MODE FOR CARRYING OUT THE INVENTION

1. Acidic Oil-In-Water-Type Emulsified Food

The acidic oil-in-water-type emulsified food of the invention contains an egg white hydrolyzate. More specifically, the acidic oil-in-water-type emulsified food of the invention can be obtained by emulsifying an aqueous phase component and an oil phase component in the presence of an emulsifier. There are no specific limitations to the emulsifier. Mayonnaise and salad dressings can be given as examples. Each component forming the acidic oil-in-water-type emulsified food of the invention will now be described.

1.1.1 Aqueous Phase Component, Oil Phase Component, and Emulsifier

Although not specifically limited, the aqueous phase component used for the acidic oil-in-water-type emulsified food of the invention may include, in addition to water, vinegars (fermented vinegars), salt, seasonings, carbohydrates, spices, artificial colors and flavorings, for example. These aqueous phase components may be used either individually or in combination of two or more.

Although not specifically limited, the oil phase component used for the acidic oil-in-water-type emulsified food of the invention may include, for example, vegetable oils and fats (for example, rapeseed oil, soybean oil, safflower oil, sunflower oil, corn oil, olive oil, grape seed oil, sesame oil, cotton seed oil, perilla seed oil, linseed oil), fish oil, liver oil, ester exchanged oils and fats, and oils and fats which mainly contain diglycerides. These oil phase components may be used either individually or in combination of two or more.

The emulsifier used for the acidic oil-in-water-type emulsified food of the invention is appropriately selected according to use from among, for example, egg yolk, egg yolk lecithin, milk proteins, soybean proteins, monoglycerides, monoglyceride derivatives, sucrose fatty acid esters, sorbitan fatty acid esters, glycerides, propylene glycol fatty acid esters, calcium stearoyl lactate, and vegetable lecithin. These emulsifiers may be used either individually or in combination of two or more. When the acidic oil-in-water-type emulsified food of the invention is mayonnaise, for example, egg yolk is preferably used as the emulsifier from the viewpoint of emulsion stability, flavor, and color tone. When the acidic oil-in-water-type emulsified food of the invention is a salad dressing, for example, egg yolk and/or the above-mentioned various types of fatty acid esters are preferably used as the emulsifier from the viewpoint of emulsion stability, flavor, and color tone.

Although there are no limitations to the amounts of the aqueous phase components and the oil phase components used in the acidic oil-in-water-type emulsified food of the invention, the mass ratio of the aqueous phase components to the oil phase components is preferably from 0.01 to 9, and more preferably from 0.1 to 5. If the mass ratio of the aqueous phase components to the oil phase components is larger than 9 or less than 0.01, it is difficult to obtain a stable acidic oil-in-water-type emulsified food.

1.1.2 Egg White Hydrolyzate

In the invention, an egg white hydrolyzate can be obtained by hydrolyzing egg white using a protease. The egg white hydrolyzate can be used in foods, feed, medical supplies, cosmetics, and the like as an antioxidant. The egg white hydrolyzate can also be used in foods, feed, medical supplies, and the like as a flavor improving agent.

The egg white hydrolyzate can be used as a raw material of the acidic oil-in-water-type emulsified food, the antioxidant, or the flavor improving agent of the invention after drying or in the form of an aqueous suspension. As a method for drying the egg white hydrolyzate, spray drying, freeze drying, and the like can be given.

As examples of the egg white used when producing the egg white hydrolyzate in the invention, raw egg white, frozen egg white, dried egg white returned with water, and egg white from which specific egg white proteins such as lysozyme have been removed can be given. Here, the raw egg white means the egg white obtained by cracking a chicken egg or the like and separating the egg yolk. Desugared egg white obtained by treating the egg white with a yeast, a bacteria, or an enzyme may also be used.

As the protease used for producing the egg white hydrolyzate in the invention, endo-propteases and exo-propteases originating from animals (for example, pepsine, chymotrypsin, trypsin, and pancreatin), vegetables (for example, papain, bromelain, and ficin), and microorganisms (for example, *Lactobacillus, Bacillus subtilis, Actinomyces*, mold, and yeast), as well as roughly purified products of these materials and fracture microorganisms, can be given. These proteases may be used either individually or in combination of two or more. In order to obtain an egg white hydrolyzate possessing an excellent antioxidant activity and flavor improving effect, it is preferable to hydrolyze egg white using a neutral protease derived from a microorganism belonging to the genus *Aspergillus*.

As the neutral protease originating from a microorganism belonging to the genus *Aspergillus*, products commercially available under the trademarks of Protease P Amano 3G™ (origin: *Aspergillus melleus*, manufactured by Amano Enzyme Inc.), Sumiteam FP™ (origin: *Aspergillus oryzae*, manufactured by Shin Nihon Chemical Co. Ltd.), and Denatyme AP™ (origin: *Aspergillus oryzae*, manufactured by Nagase ChemteX Corporation) can be given.

For example, when the egg white is hydrolyzed using a neutral protease originating from a microorganism belonging to the genus *Aspergillus*, the pH of the egg white is adjusted to 6.5 to 9.5 (preferably a pH of 7), the neutral protease originating from a microorganism belonging to the genus *Aspergillus* is added to the egg white, and the mixture is maintained at 35 to 60° C. (preferably 45 to 55° C.) for 2 to 24 hours while slowly stirring. The mixture is pasteurized, cooled, and dried by spray drying to obtain a powdery egg white hydrolyzate. The pH, temperature conditions, and cooking time are appropriately adjusted according to the types and combination of the proteases to be used.

There is no specific limitation to the acidic compound used for adjusting the pH. As examples of organic acids, acetic acid, citric acid, tartaric acid, succinic acid, and malic acid can be given. As examples of inorganic acids, hydrochloric acid, sulfuric acid, and phosphoric acid can be given. These acidic compounds may be used either individually or in combination of two or more.

In the invention, an egg white hydrolyzate can also be obtained by hydrolyzing egg white using papain. Papain is a protease extracted from papaya milk (Carica Papaya L). Use of papain can accelerate hydrolyzation of egg white.

In the invention, an egg white hydrolyzate obtained by hydrolyzing egg white using a neutral protease originating from a microorganism belong to the genus *Aspergillus* and papain is more preferable. If the egg white is hydrolyzed using only papain, the resulting egg white hydrolyzate has a strong bitter taste and, if added to the acidic oil-in-water-type emulsified food of the invention, may impair its flavor.

There are no particular limitations to the order in which the neutral protease originating from a microorganism belonging to the genus *Aspergillus* and papain are added to the egg white. Either papain may be added first or the neutral protease originating from a microorganism belonging to the genus *Aspergillus* may be added first, or it is possible to simultaneously add the neutral protease originating from a microorganism belonging to the genus *Aspergillus* and papain. It is also possible to separately use the neutral protease originating from a microorganism belonging to the genus *Aspergillus* and papain for hydrolysis.

As the papain, commercially available papains can be used, for example, Purified Papain for Foods™ manufactured by Nagase ChemteX Corporation, Papain W-40™ manufactured by Amano Enzyme Inc., Papain F™ manufactured by Higuchi Inc., and Papain™ manufactured by Solvay Co.

The egg white hydrolyzate of the invention may contain 0 to 50 mass % of a water-insoluble fraction. In other words, the egg white hydrolyzate may contain 50 to 100 mass % of a water-soluble fraction. If the amount of the water-insoluble fraction is more than 50 mass %, degradation of proteins is insufficient. Such an egg white hydrolyzate may not exhibit sufficient antioxidant effect and flavor improvement when used in an acidic oil-in-water-type emulsified food.

In the invention, the egg white hydrolyzate can exhibit such effects when it contains 0 to 50 mass % of a water-insoluble fraction. Although the details of the reason why are not certain, the water-insoluble fraction is considered to contribute to exhibition of the above effects due to a mechanism differing from that of the water-soluble fraction. Specifically, in an acidic oil-in-water-type emulsified food, the water-insoluble fraction is thought to function as a carrier of the water-soluble fraction. That is, the existence of the water-insoluble fraction in the acidic oil-in-water-type emulsified food is thought to prevent aggregation of the water-soluble fraction in the acidic oil-in-water-type emulsified food, thereby ensuring the water-insoluble fraction to exhibit the antioxidant effect and flavor improvement in the acidic oil-in-water-type emulsified food.

The water-soluble fraction and water-insoluble fraction of an egg white hydrolyzate can be separated from each other by centrifugation of a specified amount of an egg white hydrolysis solution (a solution obtained by hydrolysis using the above-mentioned enzymes). Alternatively, these fractions may be separated by adding a specified amount of egg white hydrolyzate obtained as a dry product to water, suspending the egg white hydrolyzate in water, and centrifuging the suspension. The mass ratio of these fractions in the egg white hydrolyzate can be determined by freeze-drying the solutions of each of the fractions and measuring the mass of the dried fractions.

The water-soluble fraction of the egg white hydrolyzate may contain polypeptide with an average molecular weight of about 800. On the other hand, the water-insoluble fraction of the egg white hydrolyzate may contain proteins with a molecular weight of several hundred to thirty thousand. The molecular weight of the polypeptides (proteins) contained in the water-soluble fraction and the water-insoluble fraction of an egg white hydrolyzate can be determined by a method well known to a person skilled in the art such as SDS-PAGE or calculation from formol titration.

The particle diameter of the water-insoluble fraction of an egg white hydrolyzate is 1 to 100 micrometers. The amino acid composition of the water-soluble fraction and the water-insoluble fraction of the egg white hydrolyzate mainly originate from the amino acid sequence of egg white proteins.

The egg white hydrolyzate is contained in the acidic oil-in-water-type emulsified food of the invention in an amount preferably 0.05 mass % or more, and more preferably 0.1 mass % or more. If the amount of the egg white hydrolyzate in the acidic oil-in-water-type emulsified food of the invention is less than 0.05 mass %, the effects of suppressing oxidation and inhibiting deterioration of the flavor may not be exhibited.

When the acidic oil-in-water-type emulsified food of the invention contains egg yolk, the ratio of the mass of the egg white hydrolyzate to the mass of the egg yolk solid component is preferably 0.01 or more, more preferably 0.02 to 1, and still more preferably 0.04 to 1. If the ratio of the mass of the egg white hydrolyzate to the mass of the egg yolk solid component is less than 0.01, the effects of suppressing oxidation and inhibiting deterioration of the flavor may not be exhibited. If the ratio of the mass of the egg white hydrolyzate to the mass of the egg yolk solid component is more than 1, the acidic oil-in-water-type emulsified food may have a flavor peculiar to the egg white hydrolyzate.

It is preferable that the egg white hydrolyzate possess the following characteristic: the antioxidant effect of an aqueous solution with an egg white hydrolyzate concentration of 1,000 microgram/ml which is adjusted to a pH of 4 and contains 10 mg/ml (on a solid basis) of egg yolk is equivalent to or more than the antioxidant effect of a 25 nmol/ml aqueous solution of calcium disodium ethylenediaminetetraacetate which is adjusted to a pH of 4 and contains 10 mg/ml (on a solid basis) of egg yolk.

A method for preparing each of the above aqueous solutions will now be described. First, egg yolk and egg white hydrolyzate are mixed with water to produce an aqueous solution of the egg white hydrolyzate with an egg yolk concentration of 10 mg/ml (on a solid basis) and an egg white hydrolyzate concentration of 1,000 microgram/ml, and this solution is adjusted to a pH of 4.

That is, when the aqueous solution of an egg white hydrolyzate and the aqueous solution of EDTA-Ca-2Na contain the same amount of egg yolk and have the same pH, and the egg white hydrolyzate concentration of the aqueous solution of an egg white hydrolyzate is 10 mg/ml and the EDTA-Ca-2Na concentration of the aqueous solution of EDTA-Ca-2Na is 25 nmol/ml, the antioxidant effect of the egg white hydrolyzate aqueous solution is preferred to be equivalent to or larger than the antioxidant effect of the aqueous solution of EDTA-Ca-2Na.

Next, egg yolk and calcium disodium ethylenediaminetetraacetate are mixed with water to produce an aqueous solution of calcium disodium ethylenediaminetetraacetate with an egg yolk concentration of 10 mg/ml (on a solid basis) and an EDTA-Ca-2Na concentration of 25 nmol/ml, and this solution is adjusted to a pH of 4.

Here, the antioxidant effect can be evaluated by a method commonly used for evaluating the antioxidant effect. Specifically, the antioxidant effect can be evaluated by a method described later in this specification as a method for evaluating the antioxidant effect of the acidic oil-in-water-type emulsified food of the invention.

1.1.3 Evaluation Method of Antioxidant Effect

The antioxidant effect of the acidic oil-in-water-type emulsified food and the antioxidant effect of the egg white hydrolyzate of the invention can be measured by an evaluation method known in the art, specifically by a method commonly known as a method of evaluating the oxidation of oils and fats. As the value used as the index of oxidation of oils and fats, an $O_2$ absorption amount, POV (peroxide value), a conjugated diene content, AnV (anisidine value), COV (carbonyl value), AV (acid value), an amount of amino-carbonyl reaction product, and TBARS (thiobarbituric acid reactive substance) can be given, for example (refer to FIG. 1). Among these, COV and AnV, for example, are values indicating an aldehyde content. As mentioned later in the section "5. Effect of the invention", the production of aldehydes is one of the causes of flavor degradation. Therefore, the values indicating the aldehyde content such as COV and AnV are regarded as a standard for indicating flavor degradation. The amount of amino carbonyl reaction product can also be used as an index for showing flavor degradation.

1.1.4 Evaluation Method of Flavor Improvement Factor

The flavor improvement factor of the acidic oil-in-water-type emulsified food of the invention can be measured by a sensory evaluation method. The evaluation results of the antioxidant effect mentioned above are almost correlated with the evaluation results of the flavor improvement factor. That is, there is a tendency that the smaller the antioxidant effect, the lower the flavor improvement factor. Therefore, the flavor improvement factor can be estimated from the evaluation results of the antioxidant effect.

2. Method for Producing Acidic Oil-In-Water-Type Emulsified Food

The acidic oil-in-water-type emulsified food of the invention can be prepared by a known method. For example, aqueous phase materials other than water are dispersed and/or dissolved in water or the like, oil-phase materials are added to the resulting dispersion or solution, and the mixture is stirred using a commonly used stirrer to effect preliminary emulsification, followed by emulsification using an emulsification apparatus (for example, a colloid mill) to obtain an acidic oil-in-water-type emulsified food.

When egg yolk is used as the emulsifier in producing the acidic oil-in-water-type emulsified food of the invention, in order to obtain an acidic oil-in-water-type emulsified food with excellent emulsion stability, it is desirable to first mix the aqueous phase components and the egg yolk to obtain a mixture and then to carry out emulsion by slowly adding the mixture to the oil phase components. In this case, it is a preferable to carry out emulsification after previously adding an egg white hydrolyzate to egg yolk and then to mix the aqueous phase components with the egg yolk which has been mixed with the egg white hydrolyzate. This procedure ensures production of an acidic oil-in-water-type emulsified food with more excellent emulsion stability.

3. Antioxidant

The antioxidant of the invention contains the above-mentioned egg white hydrolyzate. Specifically, the antioxidant of the invention comprises an egg white hydrolyzate obtained by treating egg white with a neutral protease originating from a microorganism belonging to the genus *Aspergillus*. As the microorganism belonging to the genus *Aspergillus*, the microorganisms given in the section "1. Acidic oil-in-water-type emulsified food" can be used. The antioxidant effect of the antioxidant of the invention can be measured by using the same method as the method for evaluating the antioxidant effect of the acidic oil-in-water-type emulsified food mentioned above.

The addition of the antioxidant of the invention to a food can improve the antioxidant properties of the food. Oils and fats are particularly oxidized easily. The oxidation of the oils and fats in food can be controlled by adding the antioxidant of the invention to the food containing the oils and fats. Oxidation can be effectively prevented by adding the antioxidant of the invention to food containing oils and fats which are particularly easily oxidized (for example, fish oil, liver oil, linseed oil, and perilla seed oil). For example, fish oil contains many components which are easily oxidized such as DHA and EPA. Liver oil contains many components which are easily oxidized such as arachidonic acid. Linseed oil and perilla seed oil contain a large amount of alpha-linolenic acid.

It is desirable to appropriately adjust the amount of the antioxidant of the invention according to the food to which the antioxidant is incorporated in a range of, for example, from 0.05 to 5 mass %.

The antioxidant of the invention may comprise an egg white hydrolyzate obtained by treating egg white with a neutral protease originating from a microorganism belonging to the genus *Aspergillus* and papain. The egg white hydrolyzate obtained by treating egg white with a neutral protease originating from a microorganism belonging to the genus *Aspergillus* and papain has a particularly excellent antioxidant affect. The method for producing an egg white hydrolyzate mentioned above can be used.

4. Flavor Improving Agent

The flavor improving agent of the invention contains the above-mentioned egg white hydrolyzate. Specifically, the flavor improving agent of the invention comprises an egg white hydrolyzate obtained by treating egg white with a neutral protease originating from a microorganism belonging to the genus *Aspergillus*. As the microorganism belonging to the genus *Aspergillus*, the microorganisms given in the section "1. Acidic oil-in-water-type emulsified food" can be used.

The flavor improving effect of the flavor improving agent of the invention can be measured using the same method as the method for evaluating the flavor improving effect of the acidic oil-in-water-type emulsified food mentioned above.

The addition of the flavor improving agent of the invention to food can improve the flavor of the food. There are a considerably large number of consumers who dislike the acidity of food containing an acid compound such as vinegar or citric acid. The acidity of the food can be suppressed and a mellow flavor can be induced by adding the flavor improving agent of the invention to such a food.

The flavor improving agent of the invention is not bitter by itself and has almost no odor. Therefore, the flavor improving agent does not impair the flavor and odor originally possessed by the food to which the flavor improving agent is added.

It is desirable to appropriately adjust the amount of the flavor improving agent of the invention according to the food to which the flavor improving agent is incorporated in a range of, for example, from 0.01 to 5 mass %.

The flavor improving agent of the invention may comprise an egg white hydrolyzate obtained by treating egg white with a neutral protease originating from a microorganism belonging to the genus *Aspergillus* and papain. The egg white hydrolyzate obtained by treating egg white with a neutral protease originating from a microorganism belonging to the genus *Aspergillus* and papain has a particularly excellent flavor improving affect due to its excellent flavor. The method for producing an egg white hydrolyzate mentioned above can be used.

5. Effect of Invention

The action and effect of the invention are described below. First, general information necessary for understanding the action and effect of the invention will be described.

5.1. Mechanism of Flavor Degradation and Emulsion Stability Degradation by Oxidation The mechanism of flavor degradation and emulsion stability degradation by oxidation in the acidic oil-in-water-type emulsified food will now be described with reference to FIG. 1.

Figure 1:
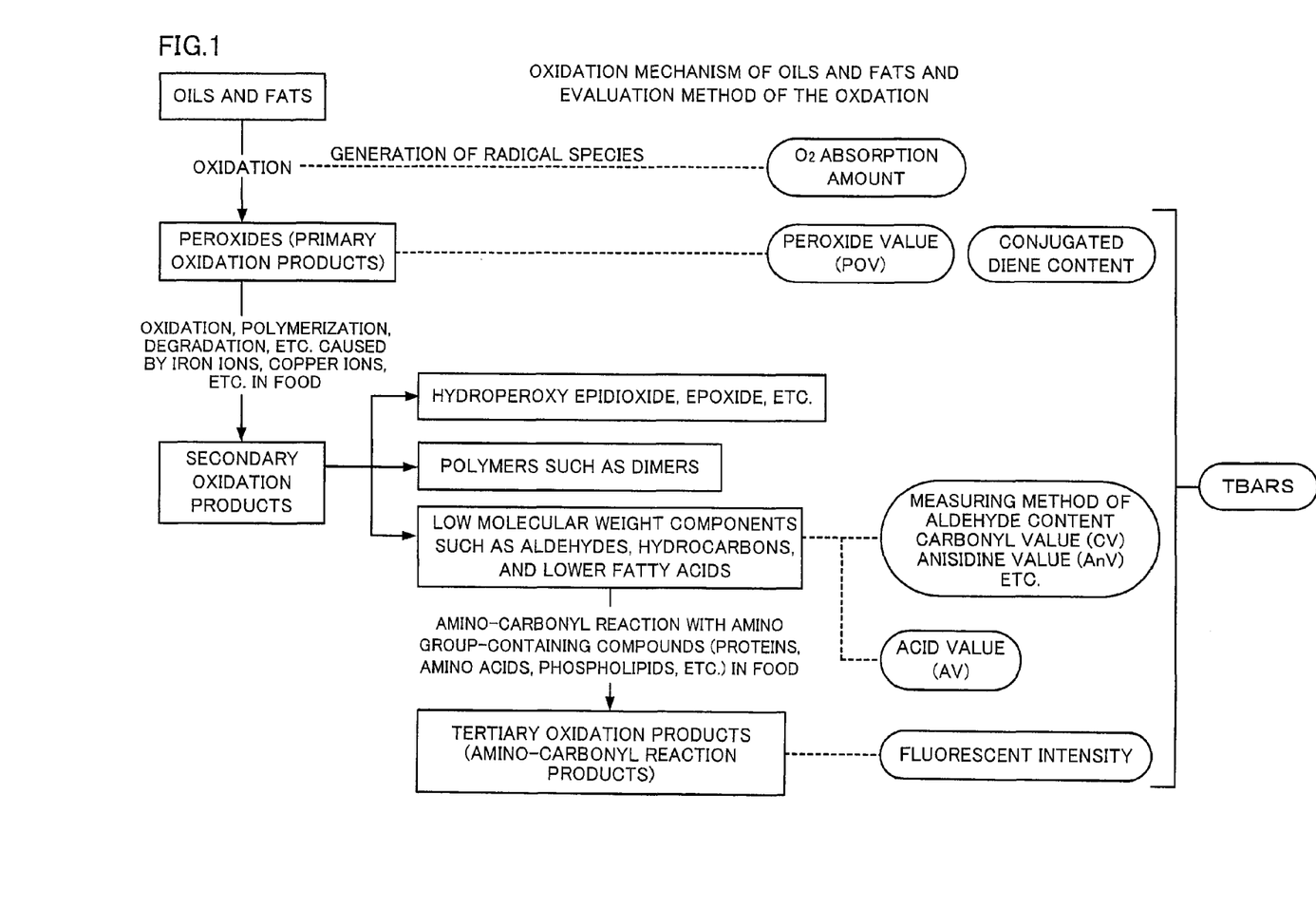
FIG. 1 is a drawing for explaining the oxidation mechanism and method for evaluating oxidation of oils and fats.

The emulsion stability of an acidic oil-in-water-type emulsified food degrades due to oxidation. Oils and fats can be given as substances causing oxidation. Oils and fats constitute the oil phase component of the acidic oil-in-water-type emulsified food.

Oils and fats are roughly classified into saturated fatty acids having only saturated bonds and unsaturated fatty acids having an unsaturated bond (a carbon-carbon double bond). In the case of unsaturated fatty acids, an auto-oxidation reaction is initiated by the production of a lipid radical which is produced by a hydrogen-drawing reaction of the unsaturated bond, whereby a peroxide (hydroperoxide; a primary oxidation product) is produced. Generally, the peroxide itself has no specific flavor or odor. However, if an ion of a metal such as copper, iron, manganese, chromium, and/or nickel, is present together with the peroxide, chain reactions consisting of (i) redox decomposition of the peroxide to further produce radicals, (ii) attack of the radicals on unsaturated bonds of the other unsaturated fatty acids, and (iii) an auto-oxidation reaction to further produce the peroxide occur. In this instance, side reactions such as polymerization of peroxides and cutting of a carbon chain to produce secondary oxidation products such as a carbonyl compound occur. This auto-oxidation reaction occurs not only in fatty acids in the same molecule, but in fatty acids in another molecule.

The carbonyl compound which is a secondary oxidation product contains aldehydes which cause flavor degradation. The aldehydes react with amino groups (amino-carbonyl reaction) such as proteins which are present near the aldehydes to produce tertiary oxidation products (amino-carbonyl reaction products). The tertiary oxidation products are also one of the substances causing a flavor change and a property change.

Particularly, when the acidic oil-in-water-type emulsified food contains egg yolk, fatty acids forming the egg yolk phospholipids are also involved in the above-mentioned auto-oxidation reaction. It is thought that the egg yolk phospholipids enclose oil drops as an emulsifier in the form of lipoproteins which are mainly combined with proteins. However, if the fatty acids of the egg yolk phospholipids are oxidized according to the above-mentioned mechanism and, as a result, if the fatty acid form and the lipophilic-hydrophilic balance change by chemical modification or carbon chain cutting, this regularity is unduly disturbed and properties of lipoproteins change accordingly. As a result, the stability of emulsion particles may be impaired. In addition, the egg yolk phospholipids converted into lipid peroxides due to oxidation increase their hydrophilic properties and exhibit a behavior of being drawn out from the oil drop interface to the aqueous phase area. As a result, the egg yolk phospholipids are more easily affected by iron ions and/or the like existing in the aqueous phase. It is thought that this phenomenon promotes production of tertiary oxidation products.

The emulsion particles becoming unstable according to the above-mentioned mechanism can barely maintain the emulsion state in a high viscosity system. However, if a physical impact, for example, is added to the container of an acidic oil-in-water-type emulsified food, it becomes impossible for the emulsion particles to maintain the emulsified state. As a result, particles of oils and fats aggregate and may be separated from the acidic oil-in-water-type emulsified food.

In particular, when the acidic oil-in-water-type emulsified food is stored in a flexible container (for example, a container made from a plastic such as polyethylene), the container must be deformed in order to remove the acidic oil-in-water-type emulsified food therefrom. Separation of components from the acidic oil-in-water-type emulsified food easily occurs on the interface of the inner surface of the container by the physical impact added to the container in such a case.

In addition, because the behavior of oxygen dissolved in the food is restricted in the case of an acidic oil-in-water-type emulsified food in a half-solid state such as mayonnaise, it is known that the degree of oxidation differs according to the location in the container. For example, the mouth and the inner surface of a bottle coming directly in contact with air immediately after opening are easily oxidized. At the interface at which the food comes in contact with the bottle, oxidation proceeds due to the air adhering to the inner surface of the bottle, the air trapped in the clearance between the bottle and the food during the filling operation, and the air invading by penetrating the bottle.

5.2. Method for Preventing Oxidation

As a method for preventing oxidation by metal ions such as iron ions and/or copper ions in food, for example, (i) a method of removing metal ions as much as possible from the raw material and (ii) a method of inactivating the metal ions existing in food can be considered.

An excellent effect of preventing oxidation can be obtained by method (i). However, method (i) degrades the food value, because the metal ions which are nutritionally important minerals are removed from the food. On the other hand, method (ii) can promote storing properties of the food while preventing flavor degradation and emulsion stability degradation since the antioxidant effect can be obtained by using this method without removing the metal ions which are nutritionally important minerals. In this respect, method (ii) is an outstanding method.

A method of adding a synthetic chelating agent (a food additive) represented by EDTA is widely known as a method particularly for inactivating iron ions and/or the like. According to this method, a strong chelating effect can be exhibited in a low pH region. For this reason, a synthetic chelating agent such as EDTA is generally used in Europe and America for preventing oxidation of an acidic oil-in-water-type emulsified food such as mayonnaise.

However, since a synthetic chelating agent generally has a strong effect, it can maintain the state of bonding with useful minerals such as calcium and/or magnesium also in human bodies. Specifically, the synthetic chelating agent inhibits these useful minerals from being absorbed in human bodies as nutritional components thus inhibiting these useful minerals from being utilized in human bodies. For this reason, the use of a synthetic chelating agent and the upper limit of the amount to be added are regulated by laws and regulations in many countries from the viewpoint of safety. In addition, consumers have a tendency of avoiding the use of chemical substances such as synthetic chelating agent in recent years.

5.3. Action and Effect of the Invention

The acidic oil-in-water-type emulsified food of the invention can inhibit the progress of oxidation due to the inclusion of an egg white hydrolyzate. Although details of the action mechanism are not known, the mechanism of inhibiting progress of oxidation is considered as follows.

It is thought that the egg white hydrolyzate forms a chelate with a metal ion such as an iron ion in the acidic oil-in-water-type emulsified food of the invention. That is, the catalytic activity of the metal ions are limited since the metal ions are captured by the egg white hydrolyzate in the acidic oil-in-water-type emulsified food of the invention, whereby production of the secondary oxidation product is interrupted in the above-mentioned oxidation mechanism and expansion of oil and fat degradation by the above-mentioned chain reaction is suppressed. As a result, the progress of oxidation can be inhibited. Furthermore, in the acidic oil-in-water-type emulsified food of the invention, the egg white hydrolyzate is thought to participate in elimination of radicals and peroxides which are produced by oxidation of oils and fats, and active oxygen generated from the radicals and peroxides. That is, since the radicals, peroxides, and active oxygen are eliminated from the acidic oil-in-water-type emulsified food of the invention by the egg white hydrolyzate, it is possible to suspend the above-mentioned chain reactions. Therefore, degradation of oils and fats can be prevented also by this mechanism.

Furthermore, since destruction of the emulsion can be prevented by inhibiting the progress of oxidation, separation of the components can be inhibited. Since the egg white hydrolyzate is derived from an egg white which is a natural food, it can be easily absorbed and digested in human bodies. For this reason, use of metal ions in human bodies is not inhibited.

The acidic oil-in-water-type emulsified food of the invention thus exhibits an outstanding antioxidant effect and is safe due to its origin from egg white which is a naturally occurring food. The acidic oil-in-water-type emulsified food of the invention excels in safety also due to its capability of inhibiting progress of oxidation without adding a chemical compound such as a synthetic chelating agent which may have an effect on human bodies.

Since the progress of oxidation can be effectively controlled even in the case in which the acidic oil-in-water-type emulsified food of the invention is stored in a flexible container or has a half-solid property, for example, separation of the components at the interface of the inner surface of the container and the food can be prevented.

Particularly when the acidic oil-in-water-type emulsified food of the invention has a pH on the acidic side and contains egg yolk, for example, when the acidic oil-in-water-type emulsified food of the invention is mayonnaise or a salad dressing, it can exhibit an outstanding effect of inhibiting the progress of oxidation. The reasons are described below.

Egg yolk contains iron ions usually at a high concentration of about 60 ppm. However, an oxidation reaction catalyzed by iron ions usually proceeds only with difficulty in egg yolk, because egg yolk has usually a pH in the range of 6 to 7 and phosphoprotein (phosvitin) contained in egg yolk forms a strong chelate with iron ions in this pH range.

However, when the acidic oil-in-water-type emulsified food of the invention contains an acidic component such as vinegar, the pH of the food is as small as 3 to 4. In this pH range, the three-dimensional structure of phosvitin changes and, as a result, a part of the iron ions forming a chelate with the phosvitin in egg yolk separate as free iron ions. This is considered to accelerate oxidation and deteriorate flavor and emulsion stability.

By contrast, in the acidic oil-in-water-type emulsified food of the invention in which iron ions are captured by the egg white hydrolyzate, the pH is on the acidic side and an outstanding effect of inhibiting the progress of oxidation can be exhibited even in the case in which the acidic oil-in-water-type emulsified food contains egg yolk.

In addition, the egg white hydrolyzate in the acidic oil-in-water-type emulsified food of the invention can inhibit deterioration of flavor and emulsion stability. An acidic oil-in-water-type emulsified food having a pH in the range of 3 to 4, such as mayonnaise or salad dressing, may lose its flavor or may have an unfavorable oxidized odor. In contrast, in the egg white hydrolyzate in the acidic oil-in-water-type emulsified food of the invention, flavor deterioration and generation of an unfavorable oxidized odor can be prevented by the oxidation inhibiting effect.

Furthermore, progress of oxidation can be effectively prevented even in the case in which the acidic oil-in-water-type emulsified food contains oils and fats which are easily oxidized (for example, fish oil, liver oil, linseed oil, and perilla seed oil).

6. EXAMPLES

The invention is described below in more detail by way of examples. In the examples, "%" refers to "mass %" unless otherwise indicated. These examples illustrate an embodiment of the invention and should not be construed as limiting the invention.

6.1. Example 1

Method of Producing Egg White Hydrolyzate

6.1.1. Preparation Example 1

180 kg of liquid egg white (manufactured by Q.P. Corporation) was charged to a tank and adjusted to a pH of 7 using citric acid. Then, 200 g of a neutral protease originating from *Aspergillus oryzae* (Sumiteam FP™ manufactured by Shin Nihon Chemical Co., Ltd.) was added to the liquid egg white and the mixture was slowly stirred at 45° C. for eight hours to treat the egg white with the enzyme. The enzyme-treated mixture was pasteurized at 97° C. for ten minutes using a kneader, cooled to 10° C. or less, and spray-dried to obtain 15.7 kg of a white powder of egg white hydrolyzate. The degree of decomposition of the resulting egg white hydrolyzate determined by formol titration was 9.9.

6.1.2. Preparation Example 2

180 kg of liquid egg white (manufactured by Q.P. Corporation) was charged to a tank and adjusted to a pH of 7 using citric acid. Then, 300 g of yeast (manufactured by Oriental Yeast Co., Ltd.) was added to the liquid egg white and the mixture was slowly stirred at 35° C. for four hours to desugar the egg white. Next, 300 g of a neutral protease originating from *Aspergillus melleus* (Protease F™ manufactured by Amano Enzyme Inc.) was added to the desugared liquid egg white and the mixture was slowly stirred at 50° C. for 12 hours to treat the egg white with the enzyme. The enzyme-treated mixture was pasteurized at 97° C. for ten minutes using a kneader, cooled to 10° C. or less, and spray-dried to obtain 16.3 kg of a white powder of egg white hydrolyzate. The degree of decomposition of the resulting egg white hydrolyzate determined by formol titration was 10.9.

6.1.3. Preparation Example 3

180 kg of liquid egg white (manufactured by Q.P. Corporation) was charged to a tank and adjusted to a pH of 7 using citric acid. Then, 300 g of yeast (manufactured by Oriental Yeast Co., Ltd.) was added to the liquid egg white and the mixture was slowly stirred at 35° C. for four hours to desugar the egg white. The mixture was heated to 65° C. and stirred at 65° C. for 30 minutes. Next, 50 g of a neutral protease originating from *Aspergillus oryzae* (Denatyme AP™ manufactured by Nagase ChemteX Corporation) and 150 g of Purified Papain for Foods™ manufactured by Nagase ChemteX Corporation were added to the desugared liquid and the mixture was slowly stirred at 55° C. for six hours to treat the egg white with the enzymes. The enzyme-treated mixture was pasteurized at 97° C. for ten minutes using a kneader, cooled to 10° C. or less, and spray-dried to obtain 13.7 kg of a white powder of egg white hydrolyzate. The degree of decomposition of the resulting egg white hydrolyzate determined by formol titration was 11.3.

6.1.4. Preparation Example 4

An enzyme-treated solution was obtained in the same manner as in Preparation Example 3, except that the treating time with the enzymes was changed from six hours to twelve hours. The resulting enzyme-treated solution was cooled to less than 10° C. and subjected to a continuous centrifugal separator to separate solid from liquid. The liquid was filtered through diatomaceous earth and the resulting transparent filtrate was spray-dried to obtain 9.9 g of a white powder. The degree of decomposition of the resulting egg white hydrolyzate determined by formol titration was 13.2.

6.1.5. Measurement of Water-Soluble Fraction and Water-Insoluble Fraction

In the above Preparation Examples 1 to 4, a prescribed amount of a solution containing the egg white hydrolyzate (the enzyme-treated solution before spray-drying) was removed and centrifuged (3,000 g×10 minutes) to separate the water-soluble fraction and the water-insoluble fraction. Each fraction obtained in the Preparation Examples 1 to 4 was freeze-dried to determine the mass ratio of each fraction relative to the total mass of the water-soluble fraction and the water-insoluble fraction.

The mass ratios of the water-soluble fractions and water-insoluble fractions in the egg white hydrolyzates obtained in the Preparation Examples 1 to 4 are shown in Table 1.

TABLE 1

| | Water-soluble fraction (mass %) | Water-insoluble fraction (mass %) |
|---|---|---|
| Preparation Example 1 | 60 | 40 |
| Preparation Example 2 | 67 | 33 |
| Preparation Example 3 | 70 | 30 |
| Preparation Example 4 (before centrifugation and filtration) | 80 | 20 |
| Preparation Example 4 (after centrifugation and filtration) | 100 | 0 |

The water-soluble fraction and water-insoluble fraction obtained from the egg white hydrolyzate of Preparation Example 3 by the above-mentioned method were analyzed using the method described above. As a result, the average molecular weight of the polypeptide contained in the water soluble fraction was about 800, whereas the molecular weight of the proteins contained in the water-insoluble fraction was from several hundreds to 30,000, showing a broad molecular weight distribution. The particle diameter of the water-insoluble fraction after drying was 1 to 100 micrometers.

6.2. Example 2

Anti-Oxidization Activity Evaluation of Egg White Hydrolyzate 6.2.1. Test Method The egg white hydrolyzate obtained in Preparation Example 2 was used in this example. Specifically, the egg white hydrolyzate obtained in Preparation Example 2 was diluted with an ion-exchanged water to obtain an egg white hydrolyzate solution with a concentration of 0.005 g/ml, which was used in the test.

An egg white and egg shell were separated from a chicken egg to obtain an egg yolk, which was diluted with ion-exchanged water to a concentration of 0.03 g/ml. This solution was pasteurized at 60° C., cooled to 10° C., and adjusted to a pH of 6.9 to obtain a diluted egg yolk solution. A part of the diluted egg yolk solution was removed and adjusted to a pH of 4.0 with glacial acetic acid (a food additive).

Figure 2:
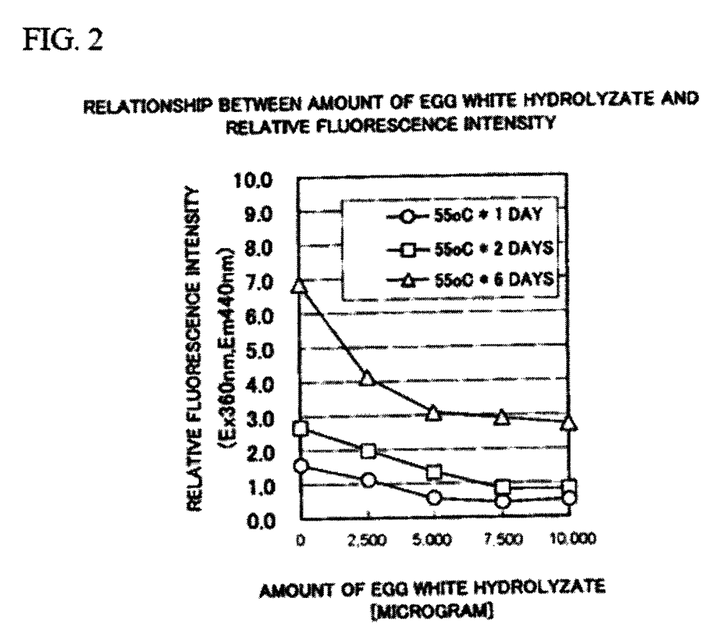
FIG. 2 shows the relationship between the amount of egg white hydrolyzate and the relative fluorescence intensity.

Screw mouth test tubes were charged with 10 ml of the test solutions according to the compositions shown in Table 2. After stirring, the test solutions were maintained at 55° C. with the screw mouths being slightly opened (to supply atmospheric air) to evaluate the progress of oxidation over time using the relative fluorescence intensity (tertiary oxidation products) as an index. The evaluation results are shown in Table 3. Based on the evaluation results shown in Table 3, the relationship between the amount of the egg white hydrolyzate and the relative fluorescence intensity is shown in FIG. 2.

EDTA-Ca-2Na used in Comparative Experimental Example 3 is a food additive (an antioxidant, Dissolvine E-CA-10™) commercially available from Maruzen Chemical Industries, Ltd.

In this example, the amount of egg yolk in each test solution was 100 mg (on a solid component basis) and the amount of iron ions contained in the egg yolk was 250 nmol. From the fact that the amount of EDTA-Ca-2Na contained in the aqueous solution of EDTA-Ca-2Na used in Comparative 3 was 250 nmol, the amount of iron ion of the egg yolk in each test solution was almost equimolar with the EDTA-Ca-2Na.

6.2.2. Evaluation Method 200 micro liters of the solution was collected in a 10 ml screw mouth test tube several times over a period of time. After the addition of a 1:3 mixed solution of diethyl ether and ethanol, the mixture was shaken to extract solid components. After centrifugation at 3,000 rpm for five minutes, a supernatant was collected and used as the sample solution.

Relative fluorescence intensity: The sample solution was put into a quartz cell and the relative fluorescence intensity was measured using a spectrophotofluorometer (U-3210™ manufactured by Hitachi, Ltd.) at Ex 360 nm and Em 440 nm. Each of the fluorescence intensity was indicated by the relative fluorescence intensity to the fluorescence intensity of a standard solution (obtained by dissolving 1 microgram of quinine sulfate in 1 ml of a 0.05 mol/l aqueous solution of sulfuric acid) which was assumed to be 1,000 when measured under the same conditions. The fluorescence intensity was measured after allowing the sample solution to stand at 55° C. for one day, two days, and six days after preparation.

6.2.3. Evaluation Results

As shown in Table 3 and FIG. 2, after allowing the sample solution to stand at 55° C. for six days, the relative fluorescence intensity of an aqueous solution with an egg white hydrolyzate concentration of 1,000 microgram/ml which was adjusted to a pH of 4 and contained 10 mg/ml (on a solid basis) of egg yolk was found to be smaller than the relative fluorescence intensity of a 25 nmol aqueous solution of calcium disodium ethylenediaminetetraacetate which was adjusted to a pH of 4 and contained 10 mg/ml (on a solid basis) of egg yolk.

The smaller the relative fluorescence intensity, the smaller the amount of tertiary oxidation products. The smaller the amount of tertiary oxidation products in a sample solution, the higher the antioxidant activity. As a result, it was shown that after allowing the sample solution to stand at 55° C. for six days, the antioxidant activity of an aqueous solution with an egg white hydrolyzate concentration of 1,000 microgram/ml which was adjusted to a pH of 4 and contained 10 mg/ml (on a solid basis) of egg yolk was equivalent to or larger than the antioxidant activity of an aqueous solution of a 25 nmol aqueous solution of calcium disodium ethylenediaminetetraacetate which was adjusted to a pH of 4 and contained 10 mg/ml (on a solid basis) of egg yolk.

TABLE 2

|  | Experimental Example | | | | Comparative Experimental Example | | |
|---|---|---|---|---|---|---|---|
|  | 1 | 2 | 3 | 4 | 1 | 2 | 3 |
| Composition of test solutions [ml] | | | | | | | |
| 0.005 g/ml egg white hydrolyzate aqueous solution | 0.50 | 1.00 | 1.50 | 2.00 | — | — | — |
| 0.115 mM EDTA-Ca—2Na solution | — | — | — | — | — | — | 2.16 |
| 0.03 g/ml diluted egg yolk solution [pH of 4] | 3.50 | 3.50 | 3.50 | 3.50 | — | 3.50 | 3.50 |
| 0.03 g/ml diluted egg yolk solution [pH of 6.9] | — | — | — | — | 3.50 | — | — |
| Ion exchange water | 6.0 | 5.50 | 5.00 | 4.50 | 6.00 | 5.50 | 4.34 |
| Total | 10.00 | 10.00 | 10.00 | 10.00 | 10.00 | 10.00 | 10.00 |
| Concentration of egg white hydrolyzate [microgram/m] | 250 | 500 | 750 | 1,000 | — | — | — |
| Concentration of EDTA-Ca—2Na [nmol/ml] | — | — | — | — | — | — | 25 |
| Proportion of egg yolk (solid basis) [mg/ml] | 10 | 10 | 10 | 10 | 10 | 10 | 10 |
| Amount of egg yolk (solid basis) [mg] | 100 | 100 | 100 | 100 | 100 | 100 | 100 |
| Amount of egg white hydrolyzate [microgram] | 2,500 | 5,000 | 7,500 | 10,000 | — | — | — |
| Egg white hydrolyzate/egg yolk (solid basis) [%] | 2.5 | 5.0 | 7.5 | 10.0 | — | — | — |

TABLE 3

| Relative fluorescence intensity | After one day | After two days | After six days |
|---|---|---|---|
| Experimental Example 1 | 1.14 | 2.01 | 4.13 |
| Experimental Example 2 | 0.58 | 1.35 | 3.10 |
| Experimental Example 3 | 0.44 | 0.84 | 2.91 |
| Experimental Example 4 | 0.54 | 0.84 | 2.75 |
| Comparative Experimental Example 1 | 0.84 | 0.17 | 0.48 |
| Comparative Experimental Example 2 | 1.57 | 2.69 | 6.88 |
| Comparative Experimental Example 3 | 0.68 | 1.18 | 3.31 |

6.3. Example 3

Anti-Oxidization Activity Evaluation of Acidic Oil-In-Water-Type Emulsified Food 6.3.1. Test Method In this example, egg yolk-type mayonnaises were prepared as the acidic oil-in-water-type emulsified food in Experimental Examples 5 to 8 and Comparative Experimental Examples 4 and 5. The raw material compositions of the acidic oil-in-water-type emulsified foods in the Experimental Examples and Comparative Experimental Examples are shown in Table 4. Anti-oxidization activity of the acidic oil-in-water-type emulsified foods prepared were evaluated.

The egg white hydrolyzate prepared in Preparation Example 2 of Example 1 was used. EDTA-Ca-2Na used in Comparative Experimental Example 5 was a food additive (an antioxidant, Dissolvine E-CA-10™), commercially available from Maruzen Chemical Industries, Ltd.

In Experimental Examples 5, 6, 7, and 8, the egg white hydrolyzate was added in an amount corresponding 2%, 10%, 20%, and 30% of the amount of the egg yolk solid component respectively. In Comparative Experimental Example 4, the egg yolk was added in an amount corresponding to 4.5% (on a solid basis) of the total amount of the raw materials. In Comparative Experimental Example 5, EDTA-Ca-2Na was added in an amount corresponding to 0.01% of the total amount of the raw materials (corresponding to 0.22% of the egg yolk solid component).

In Table 4, 10% salted egg yolk was an egg yolk to which salt was added at a mass ratio of the egg yolk to salt of 9:1. Vinegar with an acidity of 4% was used.

TABLE 4

|  | Experimental Example | | | | Comparative Experimental Example | |
|---|---|---|---|---|---|---|
| Composition (g) | 5 | 6 | 7 | 8 | 4 | 5 |
| Edible vegetable oil * | 7500 | 7500 | 7500 | 7500 | 7500 | 7500 |
| 10% salted egg yolk | 1,000 | 1,000 | 1,000 | 1,000 | 1,000 | 1,000 |
| Vinegar | 1,411 | 1,375 | 1,330 | 1,285 | 1,420 | 1,419 |
| Salt | 50 | 50 | 50 | 50 | 50 | 50 |
| Sodium glutamate | 30 | 30 | 30 | 30 | 30 | 30 |
| Mustard powder | 0.6 | 0.6 | 0.6 | 0.6 | 0.6 | 0.6 |
| Egg white hydrolyzate | 9 | 45 | 90 | 135 | 0 | 0 |
| EDTA | 0 | 0 | 0 | 0 | 0 | 1 |
| Total | 10,000.6 | 10,000.6 | 10,000.6 | 10,000.6 | 10,000.6 | 10,000.6 |
| pH of product | 3.98 | 4.03 | 4.12 | 4.20 | 3.93 | 3.98 |

* The edible vegetable oil was a 1:1 mixture of rapeseed oil and soybean oil.

Among the components shown in Table 4, the egg white hydrolyzate and 10% salted egg yolk were mixed, provided that only 10% salted egg yolk was used in Comparative Experimental Example 4 and EDTA-Ca-2Na was used instead of the egg white hydrolyzate in Comparative Experimental Example 5. Then, salt, vinegar, and sodium glutamate were added to the mixture. Then, the edible vegetable oil and the mustard powder were added, and the mixtures were preliminary emulsified using a Hobart mixer. The preliminarily emulsified mixtures were further processed using a colloid mill to obtain acidic oil-in-water-type emulsified foods (egg yolk-type mayonnaises).

After 200 g nylon polyethylene bags were filled with the resulting acidic oil-in-water-type emulsified foods and sealed, they were allowed to stand in a shaded place at 55° C. for 7 days.

6.3.2. Evaluation Method

After standing for seven days, the acidic oil-in-water-type emulsified foods prepared in Experimental Examples 5 to 8 and Comparative Experimental Examples 4 and 5 were subjected to an antioxidant activity evaluation and a sensory evaluation according to the following procedures.

i) Auto-Oxidation Index

Lipid components were extracted from the acidic oil-in-water-type emulsified food after standing for seven days using a common Bligh and Dyer method. The extracts were used as test solutions.

i-1) Peroxide Value (POV)

As mentioned above, the peroxide value was used as an index for production of the primary oxidation products (refer to FIG. 1). In this example, the peroxide value (POV) of the test solutions was measured by the electric potential-coulometric method using a POV meter (IP200™ manufactured by Iijima Electronics Corporation).

i-2) Anisidine Value

As mentioned above, the anisidine value is used as an index for production of the secondary oxidation products shown in FIG. 1 (refer to FIG. 1). In this Example, the anisidine value was measured according to the standard method for testing oils and fats 23.5-1996.

ii) Sensory Evaluation

The mayonnaises after standing for seven days were evaluated by 15 panelists. The flavor of each sample was evaluated based on the standard in which a control sample preserved in a shaded place at 5° C. for 7 days was given a score of 7. That is, the higher the score of the sensory evaluation, the smaller the deterioration degree of the flavor.

6.3.3. Evaluation Results

The resulting POV and anisidine values are shown in Table 5 and the results of sensory evaluation are shown in Table 6.

TABLE 5

Evaluation of oxidation (POV and anisidine values)

| | Experimental Example | | | | Comparative Experimental Example | |
|---|---|---|---|---|---|---|
| | 5 | 6 | 7 | 8 | 6 | 7 |
| EDTA * | — | — | — | — | — | 0.22% |
| Egg white hydrolyzate * | 2% | 10% | 20% | 30% | — | — |
| POV (meq/kg) | 3.3 | 2.7 | 1.9 | 1.8 | 5.7 | 2.4 |
| Anisidine value | 3.9 | 3.4 | 2.6 | 2.4 | 7.2 | 1.4 |

* The amount added relative to egg yolk solid component

It can be seen from Table 5 that the increase of the POV (primary oxidation products) and the anisidine value (secondary oxidation products) was controlled during standing of the acidic oil-in-water-type emulsified foods of Experimental Examples 5 to 8 due to inclusion of the egg white hydrolyzate. The antioxidant effect was dependent on the concentration of the egg white hydrolyzate.

The acidic oil-in-water-type emulsified foods of Experimental Examples 6 and 7, which contained the egg white hydrolyzate in an amount corresponding to 10% and 20% of the egg yolk solid component respectively, exhibited the same degree of antioxidant effect as the acidic oil-in-water-type emulsified food of Comparative Experimental Example 7. The acidic oil-in-water-type emulsified food of Comparative Experimental Example 7 contained EDTA in an amount corresponding to 0.22% of the egg yolk solid component, which is close to the concentration of EDTA in commercially available mayonnaises (about 75 mg of EDTA per 1 kg of mayonnaise).

TABLE 6

Sensory Evaluation

| | Experimental Example | | | | Comparative Experimental Example | |
|---|---|---|---|---|---|---|
| | 5 | 6 | 7 | 8 | 6 | 7 |
| EDTA * | — | — | — | — | — | 0.22% |
| Egg white hydrolyzate * | 2% | 10% | 20% | 30% | — | — |
| Flavor (score) | 4.3 | 5.8 | 5.6 | 4.9 | 2.5 | 5.5 |

* The amount added in each sample

It can be seen from Table 6 that the flavor of the acidic oil-in-water-type emulsified foods of Experimental Examples 5 to 8 can be improved and prevented from being deteriorated due to inclusion of the egg white hydrolyzate.

The acidic oil-in-water-type emulsified food of Experimental Example 6 exhibited the highest flavor evaluation. Specifically, the acidic oil-in-water-type emulsified food of Experimental Example 6 obtained higher flavor evaluation results than the acidic oil-in-water-type emulsified food of Comparative Experimental Example 7. The results of these experiments confirmed that when the amount of the egg white hydrolyzate added is 10% of the egg yolk solid component, the acidic oil-in-water-type emulsified food of the invention not only exhibits the effect of preventing flavor deterioration, but also exhibits effects of increasing richness of flavor and controlling acidic taste (the effect of easing bitter taste of a vinegar into a mild taste).

The same evaluation as in this example was carried out by adding the egg white hydrolyzate in an amount corresponding to 1% of the egg yolk solid component in preparing the acidic oil-in-water-type emulsified food of Experimental Example 5. As a result, the same result was obtained with respect to the anti-oxidization property. As for the flavor, although a slight flavor peculiar to egg white was sensed, the acidic oil-in-water-type emulsified food had a good taste.

6.4. Example 4

Method of Producing Acidic Oil-In-Water-Type Emulsified Food

The acidic oil-in-water-type emulsified food containing fish oil of Example 4 was prepared in the same manner as the method of preparing the acidic oil-in-water-type emulsified foods of Experimental Examples 5 to 8, except that among the components in Experimental Example 6 of Example 3, 7,500 g of edible vegetable oil was replaced with 6,500 g of rapeseed oil and 1,000 g of purified fish oil. The purified fish oil used in this Example contained 25% DHA and 12% EPA, and its omega-3 (n-3) fatty acid content was about 40% (for example, the oil contains about 600 mg of omega-3 fatty acids per 15 g of mayonnaise).

The resulting acidic oil-in-water-type emulsified food was packed in small aluminum bags (15 g for each) and allowed to stand at room temperature for three months. The bags were opened to check the flavor. As a result, it was confirmed that the flavor was good with no smell of fish due to deterioration by oxidation.

Based on the above results, the acidic oil-in-water-type emulsified food of Example 4 was confirmed to exhibit an antioxidant effect due to the egg white hydrolyzate contained therein, even if the food contains easily oxidized components such as EPA and DHA.

The same evaluation was carried out by adding the egg white hydrolyzate such that the ratio of the mass of the egg white hydrolyzate to the mass of the egg yolk solid component is 1 in preparing the acidic oil-in-water-type emulsified food of this Example. As a result, the same result was obtained with respect to the anti-oxidation property. As for the flavor, although a slight flavor peculiar to egg white was sensed, the acidic oil-in-water-type emulsified food had a good flavor.

6.5. Example 5

Method of Producing Acidic Oil-In-Water-Type Emulsified Food 6.5.1. Test Method In this Example, emulsion salad dressings (containing egg yolk) were prepared as the acidic oil-in-water-type emulsified foods in Experimental Examples 9 and 10 and Comparative Experimental Examples 8 and 9. The raw material compositions of the acidic oil-in-water-type emulsified foods in the Experimental Examples and Comparative Experimental Examples are shown in Table 7. Anti-oxidization activity of the emulsion salad dressings prepared was evaluated.

The egg white hydrolyzate prepared in Preparation Example 2 of Example 1 was used. EDTA-Ca-2Na used in Comparative Experimental Example 9 was a food additive (an antioxidant, Dissolvine E-CA-10™) commercially available from Maruzen Chemical Co., Ltd.

In Experiment Examples 9 and 10 and Comparative Experimental Examples 8 and 9, the egg yolk was added in an amount corresponding to 0.45% (on a solid basis) of the total amount of the raw materials. The egg white hydrolyzate in an amount corresponding to 11% and 44% of the egg yolk solid component was added to the acidic oil-in-water-type emulsified foods of Experimental Examples 9 and 10 respectively. EDTA-Ca-2Na in an amount corresponding to 0.01% of the total amount of the raw materials (corresponding to 2.2% of the egg yolk solid component) was added to the acidic oil-in-water-type emulsified food of Comparative Experimental Example 9.

In Table 6, the same 10% salted egg yolk, mustard powder, and vinegar as those used in Example 3 were used. A product available under the trademark of Echo Gum™ (manufactured by Dainippon Pharmaceutical Co., Ltd.) was used as a xanthan gum.

The amount of the egg white hydrolyzate relative to the total amount of the raw material and the amount of the egg yolk solid component, and the amount of EDTA relative to the total amount of the raw material and the amount of the egg yolk solid component are shown in Table 8.

TABLE 7

| Composition [g] | Experimental Example | | Comparative Experimental Example | |
|---|---|---|---|---|
| | 9 | 10 | 8 | 9 |
| Edible vegetable oil* | 4,000 | 4,000 | 4,000 | 4,000 |
| 10% salted egg yolk | 100 | 100 | 100 | 100 |
| MSG | 50 | 50 | 50 | 50 |
| Salt | 350 | 350 | 350 | 350 |
| Vinegar | 700 | 700 | 700 | 700 |
| Glucose-fructose solution | 500 | 500 | 500 | 500 |
| Mustard powder | 0.6 | 0.6 | 0.6 | 0.6 |
| Xanthan gum | 20 | 20 | 20 | 20 |
| Pure water | 4,300 | 4,300 | 4,300 | 4,300 |
| Egg white hydrolyzate | 5 | 20 | 0 | 0 |
| EDTA | 0 | 0 | 0 | 1 |
| Total | 10,020.6 | 10,021.6 | 10,025.6 | 10,040.6 |
| pH | 3.66 | 3.70 | 3.67 | 3.68 |

*The edible vegetable oil was rapeseed oil.

TABLE 8

| | Experimental Example | | Comparative Experimental Example | |
|---|---|---|---|---|
| | 9 | 10 | 8 | 9 |
| Egg yolk solid component | 45 | 45 | 45 | 45 |
| EDTA | 0 | 0 | 0 | 0 |
| Egg white hydrolyzate | 5 | 20 | 0 | 1.0 |
| Amount (%) relative to egg yolk solid component | | | | |
| EDTA | 0 | 0 | 0 | 2.2 |
| Egg white hydrolyzate | 11 | 44 | 0 | 0 |
| Amount (%) relative to total mass of raw materials | | | | |
| EDTA | 0 | 0 | 0 | 0.01 |
| Egg white hydrolyzate | 0.05 | 0.20 | 0 | 0 |

Among the components shown in Table 7, the egg white hydrolyzate, sucrose fatty acid ester, MSG, and 10% salted egg yolk were mixed, provided that only 10% salted egg yolk was used in Comparative Experimental Example 8 and EDTA-Ca-2Na was used instead of the egg white hydrolyzate in Comparative Experimental Example 9. The remaining raw material components were added to the mixtures and the resulting mixtures were emulsified using a simple mixer to obtain acidic oil-in-water-type emulsified foods (emulsion salad dressings).

After 200 g glass bottles were filled with the obtained acidic oil-in-water-type emulsified foods and sealed, they were allowed to stand in a shaded place at 25° C. for four months.

6.5.2. Evaluation Method

After standing for four months, the acidic oil-in-water-type emulsified foods prepared in Experimental Examples 9 and 10 and Comparative Experimental Examples 8 and 9 were subjected to an antioxidant activity evaluation and a sensory evaluation according to the following procedures.

i) Auto-Oxidation Index (Peroxide Value (POV))

Lipid components were extracted from the acidic oil-in-water-type emulsified foods which were allowed to stand for four months in the same manner as in Example 3 to use the extracted lipid components as a test solution. The peroxide value (POV) was measured using this test solution.

ii) Sensory Evaluation

The mayonnaises after standing for four months were evaluated by 8 panelists.

The flavor of each sample was evaluated based on the standard in which a control sample preserved in a shaded place at 5° C. for 7 days was given a score of 7. That is, the higher the score of the sensory evaluation, the smaller the deterioration degree of the flavor.

6.5.3. Evaluation Results

The results of POV measurement are shown in Table 9 and the results of sensory evaluation are shown in Table 10.

TABLE 9

|  | Experimental Example | | Comparative Experimental Example | |
|---|---|---|---|---|
|  | 9 | 10 | 8 | 9 |
| POV | 0.3 | 0.2 | 1.1 | 0.8 |

TABLE 10

|  | Experimental Example | | Comparative Experimental Example | |
|---|---|---|---|---|
|  | 9 | 10 | 8 | 9 |
| Result of sensory evaluation | 3.8 | 5.1 | 2.5 | 5.3 |

The above results confirmed that the acidic oil-in-water-type emulsified foods having a lower POV were obtained in Experimental Examples 9 and 10 as compared with the acidic oil-in-water-type emulsified foods of Comparative Experimental Examples 8 and 9 due to inclusion of an egg white hydrolyzate. The above results confirmed that the acidic oil-in-water-type emulsified foods exhibiting better sensory evaluation results were obtained in Experimental Examples 9 and 10 as compared with the acidic oil-in-water-type emulsified foods of Comparative Experimental Examples 8 and 9 due to inclusion of an egg white hydrolyzate. In this manner, the antioxidant effect and flavor deterioration inhibiting effect (flavor improving effect) of the egg white hydrolyzate in acidic oil-in-water-type emulsified foods of Experimental Examples 9 and 10 were confirmed.

It can be understood from the results of Experimental Examples 9 and 10 shown in Tables 8 to 10 that the acidic oil-in-water-type emulsified foods exhibit an outstanding antioxidant effect and flavor deterioration inhibiting effect (flavor improving effect), particularly when the foods contain 0.05 mass % or more (more preferably 0.2 mass % or more) of the egg white hydrolyzate.

6.6. Example 6

Method of Producing Acidic Oil-In-Water-Type Emulsified Food 6.6.1. Test Method and Evaluation Method In this Example, emulsion salad dressings not containing egg yolk were prepared as the acidic oil-in-water-type emulsified foods in Experimental Examples 11 and 12 and Comparative Experimental Examples 10 and 11. More specifically, the experiments were carried out in the same manner and under the same conditions as in Example 5, except for replacing 100 g of 10% salted egg yolk with 40 g of a sucrose fatty acid ester (S-1670™ (HLB=16) manufactured by Mitsubishi-Kagaku Foods Corporation). That is, except for replacing 100 g of 10% salted egg yolk with 40 g of a sucrose fatty acid ester, Experimental Example 11 of this Example was the same as Experimental Example 9 of Example 5, Experimental Example 12 of this Example was the same as Experimental Example 10 of Example 5, Comparative Experimental Example 10 of this Example was the same as Comparative Experimental Example 8 of Example 5, and Comparative Experimental Example 11 of this Example was the same as Comparative Experimental Example 9 of Example 5.

Anti-oxidization activity of the emulsion salad dressings prepared was evaluated in the same manner as in Example 5.

6.6.2. Evaluation Results

The results of POV measurement are shown in Table 11 and the results of sensory evaluation are shown in Table 12.

TABLE 11

|  | Experimental Example | | Comparative Experimental Example | |
|---|---|---|---|---|
|  | 11 | 12 | 10 | 11 |
| POV | 0.5 | 0.4 | 1.3 | 0.5 |

TABLE 12

|  | Experimental Example | | Comparative Experimental Example | |
|---|---|---|---|---|
|  | 11 | 12 | 10 | 11 |
| Result of sensory evaluation | 4.1 | 5.9 | 3.4 | 6.0 |

The above results confirmed that the acidic oil-in-water-type emulsified foods obtained in Experimental Examples 11 and 12 had a POV lower than the acidic oil-in-water-type emulsified food of Comparative Experimental Example 10 and equivalent to the acidic oil-in-water-type emulsified food of Comparative Experimental Example 11 due to inclusion of an egg white hydrolyzate. In addition, the acidic oil-in-water-type emulsified foods obtained in Experimental Examples 11 and 12 exhibited better sensory evaluation results as compared with the acidic oil-in-water-type emulsified food of Comparative Experimental Example 10 due to inclusion of an egg white hydrolyzate. Thus, the antioxidant effect and flavor deterioration inhibiting effect (flavor improving effect) of the egg white hydrolyzate in acidic oil-in-water-type emulsified foods of Experimental Examples 11 and 12 were confirmed.

It can be understood from the results of Experimental Examples 11 and 12 shown in Tables 11 to 12 that the acidic oil-in-water-type emulsified foods exhibit an outstanding antioxidant effect and flavor deterioration inhibiting effect (flavor improving effect), particularly when the foods contain 0.05 mass % or more (more preferably 0.2 mass % or more) of egg white hydrolyzate.

The invention claimed is:

1. An acidic oil-in-water-type emulsified food comprising:
    an edible vegetable oil, a vinegar, and an egg white hydrolyzate comprising 20 to 50 mass % of a water-insoluble fraction; and
    egg yolk,
    wherein a ratio of the mass of the egg white hydrolyzate to a mass of the egg yolk as solid component is 0.1 to 1,
    wherein the content of the egg white hydrolyzate is 0.05 mass % or more, and
    wherein the acidic oil-in-water-type emulsified food does not comprise a beta-glucan.

2. The acidic oil-in-water-type emulsified food as defined in claim 1, wherein the egg white hydrolyzate is obtained by treating egg white with a neutral protease originating from a microorganism belonging to the genus *Aspergillus*.

3. The acidic oil-in-water-type emulsified food as defined in claim 1, wherein the egg white hydrolysate is obtained by treating egg white with a neutral protease originating from a microorganism belonging to the genus *Aspergillus* and papain.

4. The acidic oil-in-water-type emulsified food as defined in claim 1, having the following characteristic: an antioxidant effect of 1,000 microgram/ml of an aqueous solution of the egg white hydrolyzate which is adjusted to a pH of 4 and contains 10 mg/ml (on a solid basis) of egg yolk is equivalent to or more than an antioxidant effect of a 25 nmol/ml aqueous solution of calcium disodium ethylenediaminetetraacetate which is adjusted to a pH of 4 and contains 10 mg/ml (on a solid basis) of the egg yolk.

5. The acidic oil-in-water-type emulsified food as defined in claim 1, wherein a particle diameter of the water-insoluble fraction is 1 to 100 micrometers.

6. The acidic oil-in-water-type emulsified food as defined in claim 2, wherein the treating the egg white with the neutral protease originating from a microorganism belonging to the genus *Aspergillus* is performed at a pH of 6.5 to 9.5 and at a temperature of 35 to 60° C. for 2 to 24 hours.

7. The acidic oil-in-water-type emulsified food as defined in claim 1, wherein the content of the egg white hydrolyzate is 0.05 to 4.5 mass %.

8. The acidic oil-in-water-type emulsified food as defined in claim 1, not comprising a synthetic chelating agent.

9. The acidic oil-in-water-type emulsified food as defined in claim 1, not comprising an ethylenediaminetetraacetate or its salt.

10. The acidic oil-in-water-type emulsified food as defined in claim 1, wherein a pH of the acidic oil-in-water-type emulsified food is 3 to 4.

11. The acidic oil-in-water-type emulsified food as defined in claim 10, wherein a part of iron ions comprised in the egg yolk separate as free iron ions.

12. The acidic oil-in-water-type emulsified food as defined in claim 1, wherein aqueous phase components to oil phase components before emulsification is 0.01 to 9.

13. The acidic oil-in-water-type emulsified food as defined in claim 12, wherein aqueous phase components to oil phase components before emulsification is 0.1 to 5.

14. The acidic oil-in-water-type emulsified food as defined in claim 1, wherein a degree of decomposition of the egg white hydrolyzate determined by formol titration is 9.9 to 13.2.

15. The acidic oil-in-water-type emulsified food as defined in claim 7, wherein the content of the egg white hydrolyzate is 0.45 to 1.35 mass %.

16. The acidic oil-in-water-type emulsified food as defined in claim 1, wherein the egg white hydrolyzate comprises 50 to 80 mass % of a water-soluble fraction.

17. The acidic oil-in-water-type emulsified food as defined in claim 16, wherein the water-soluble fraction of the egg white hydrolyzate comprises a protein having an average molecular weight of about 800.

18. The acidic oil-in-water-type emulsified food as defined in claim 1, wherein progress of oxidation is prevented without a synthetic chelating agent.

19. The acidic oil-in-water-type emulsified food as defined in claim 1, wherein flavor deterioration is prevented without a synthetic chelating agent.

20. The acidic oil-in-water-type emulsified food as defined in claim 14, wherein a degree of decomposition of the egg white hydrolyzate determined by formol titration is 9.9 to 11.3.

* * * * *